United States Patent
Uchida et al.

(10) Patent No.: US 10,481,169 B2
(45) Date of Patent: Nov. 19, 2019

(54) DIAGNOSTIC METHOD AND BIOMARKER FOR LIFESTYLE DISEASE

(71) Applicants: TOYOTA JIDOSHA KABUSHIKI KAISHA, Toyota-shi, Aichi-ken (JP); NATIONAL UNIVERSITY CORPORATION NAGOYA UNIVERSITY, Nagoya-shi, Aichi-ken (JP)

(72) Inventors: Koji Uchida, Nagoya (JP); Takahiro Shibata, Nagoya (JP); Kenji Ishikawa, Nagoya (JP); Oi Lun Helena Li, Nagoya (JP); Tadashi Matsushita, Nagoya (JP); Ryosuke Kikuchi, Nagoya (JP); Junzo Ukai, Nagoya (JP)

(73) Assignees: TOYOTA JIDOSHA KABUSHIKI KAISHA, Nagoya-shi, Aichi-ken (JP); NATIONAL UNIVERSITY CORPORATION NAGOYA UNIVERSITY, Nagoya-shi, Aichi-ken (JP)

(*) Notice: Subject to any disclaimer, the term of this patent is extended or adjusted under 35 U.S.C. 154(b) by 0 days.

(21) Appl. No.: 15/906,032

(22) Filed: Feb. 27, 2018

(65) Prior Publication Data

US 2018/0246129 A1    Aug. 30, 2018

(30) Foreign Application Priority Data

Feb. 28, 2017  (JP) ................... 2017-036997

(51) Int. Cl.
*G01N 33/92* (2006.01)
*H01J 49/00* (2006.01)
(Continued)

(52) U.S. Cl.
CPC .......... *G01N 33/92* (2013.01); *H01J 49/0027* (2013.01); *H01J 49/165* (2013.01);
(Continued)

(58) Field of Classification Search
CPC ............... G01N 33/92; G01N 2405/00; G01N 2560/00; G01N 2800/042;
(Continued)

(56) References Cited

U.S. PATENT DOCUMENTS

2007/0155747 A1* 7/2007 Dasse ................... C07C 271/44
514/235.5
2011/0315868 A1* 12/2011 Hirabayashi ............ H01J 9/004
250/282

FOREIGN PATENT DOCUMENTS

| JP | 2003-130868 A | 5/2003 |
| JP | 2010-151800 A | 7/2010 |
| KR | 10-2015-0074759 A | 7/2015 |

* cited by examiner

*Primary Examiner* — Nicole M Ippolito
(74) *Attorney, Agent, or Firm* — Sughrue Mion, PLLC (57) ABSTRACT

Provided is a novel method and the like for diagnosing a lifestyle disease. The method for diagnosing a lifestyle disease provided by the present invention includes: collecting a biological sample from a subject; measuring the concentration of a fatty acid amide contained in the biological sample; determining whether the subject suffers from a lifestyle disease or a lifestyle disease has progressed when the measured value of the concentration of the fatty acid amide in the sample obtained from the subject is lower than a measurement result obtained from a healthy subject.

6 Claims, 4 Drawing Sheets

(51) Int. Cl.
*H01J 49/42* (2006.01)
*H01J 49/16* (2006.01)

(52) U.S. Cl.
CPC ...... *H01J 49/4215* (2013.01); *G01N 2405/00* (2013.01); *G01N 2560/00* (2013.01); *G01N 2800/042* (2013.01); *G01N 2800/044* (2013.01)

(58) Field of Classification Search
CPC ............ G01N 2800/044; H01J 49/0027; H01J 49/165; H01J 49/4215
USPC ................................ 250/281, 282, 283, 288
See application file for complete search history.

DIAGNOSTIC METHOD AND BIOMARKER FOR LIFESTYLE DISEASE

CROSS-REFERENCE

The priority claim for this application is based on Japanese Patent Application No. 2017-036997 submitted on Feb. 28, 2017. The entire contents of that application are incorporated by reference in the present Description.

BACKGROUND OF THE INVENTION

1. Field of the Invention

The present invention relates to a method for diagnosing a lifestyle disease, and to a biomarker for use in the method.

2. Description of the Related Art

As lifestyles and social environments change, the number of patients suffering from lifestyle diseases is increasing year by year. Lifestyle diseases are a group of diseases the onset and progress of which are associated with lifestyle factors such as eating habits, exercise habits, rest, smoking and alcohol consumption, and typical examples include non-insulin-dependent diabetes (hereunder simply called diabetes), dyslipidemia (also called hyperlipidemia), high blood pressure, inflammatory disease and the like. At present, lifestyle diseases are mainly treated by treating the symptoms, but since lifestyle diseases have few subjective symptoms, a disease may progress undetected and cause damage to the brain, heart, blood vessels and the like. For example, once diabetes has developed it can cause complications such as retinopathy, and may promote the development of cardiovascular diseases such as ischemic heart disease and stroke. Consequently, diagnosing lifestyle diseases in the early stages and preventing their subsequent progress is considered a serious issue. Conventional techniques for diagnosing lifestyle diseases are described for example in Japanese Patent Application Laid-open No. 2010-151800 and Japanese Patent Application Laid-open No. 2003-130868.

Meanwhile, the use of treatments that are matched appropriately to the individual patient's symptoms has recently become more popular in the medical field, whether for lifestyle diseases or other diseases. From the standpoint of improving quality of life (QOL), moreover, there is also demand for tailor-made therapies that combine common therapies with therapies matched to the individual patient's symptoms. Consequently, there is also demand for diagnostic methods that can take various factors into account when diagnosing lifestyle diseases for example. As one example, it is especially desirable to diagnose a disease at a relatively early stage before the condition has progressed.

SUMMARY OF THE INVENTION

In light of these circumstances, it is an object of the present invention to provide a novel method and the like for diagnosing (screening) a lifestyle disease. It is another object to provide a novel biomarker useful for diagnosing a lifestyle disease.

The inventors have conducted exhaustive research into acylates of long chain fatty acids, which are attracting attention as novel lipid mediators since they are present in the living body and have a variety of physiological activities. As a result, we perfected the present invention after discovering that of the long-chain fatty acid acylates, the fatty acid amides are present in relatively low concentrations in vivo in hyperlipidemia patients in comparison with healthy subjects.

That is, the invention disclosed here provides a method for diagnosing a lifestyle disease. This method for diagnosing a lifestyle disease includes: collecting a biological sample from a subject; measuring the concentration of a fatty acid amide contained in the biological sample; and determining whether the subject suffers from a lifestyle disease or a lifestyle disease has progressed when the measured value of the concentration of the fatty acid amide obtained from the subject is lower than a measurement result obtained from a healthy subject.

With this configuration, the concentration of a fatty acid amide is measured in a biological sample from a test subject. Based on the measured value of this oleamide concentration, it is then possible to judge whether the subject suffers from a lifestyle disease or whether a lifestyle disease has progressed. Thus, a novel method for diagnosing a lifestyle disease is provided using a biological compound (fatty acid amide) as a biomarker for the lifestyle disease.

In a preferred embodiment of the diagnostic method disclosed here, the biological sample is an organ or blood. Because blood is relatively easy to collect and can be easily obtained in the course of other testing, diagnosis can be carried out without placing an extra burden on the patient when measuring the concentration of the fatty acid amide. However, the specimen for measuring the fatty acid amide concentration is not restricted to blood, and measurement can be carried out for example even if the specimen is an organ or the like. It is thus possible to diagnose a lifestyle disease by a variety of testing techniques.

In a preferred embodiment of the diagnostic method disclosed here, the concentration of the fatty acid amide is measured by liquid chromatography-mass spectrometry. The liquid chromatography-mass spectrometry method preferably includes: isolating two or more components contained in the biological sample by liquid chromatography; ionizing the isolated components, selecting a specific mass component with a quadrupole mass spectrometer, then dissociating the specific mass component; and detecting the dissociated component with a mass spectrometer. With this configuration, it is possible to measure the concentration of a fatty acid amide with a high degree of precision, and thus to precisely diagnose a lifestyle disease.

In a preferred embodiment of the diagnostic method disclosed here, the lifestyle disease is at least one selected from the group consisting of obesity, dyslipidemia, diabetes and impaired glucose tolerance. Fatty acid amide concentrations exhibit a relatively high correlation with glucose concentrations for example. Consequently, of the lifestyle diseases, it is especially desirable to use this diagnostic method to diagnose obesity, dyslipidemia, diabetes and impaired glucose tolerance.

In a preferred embodiment of the diagnostic method disclosed here, the fatty acid amide is oleamide. The existence and progress of a lifestyle disease can thus be more accurately reflected in the concentration of the fatty acid amide, and the lifestyle disease can be diagnosed more reliably.

BRIEF DESCRIPTION OF THE DRAWINGS

For a better understanding of the invention as well as other objects and further features thereof, reference is made to the following detailed description to be read in connection with the accompanying drawings.

DETAILED DESCRIPTION OF THE PREFERRED EMBODIMENTS

Preferred embodiments of the present invention are explained below. Matters other than those specifically mentioned in this Description that are necessary for implementing the present invention can be understood as design matters by a person skilled in the art based on prior art in the field. The present invention can be implemented based on the content disclosed in this Description and in the drawings, and on technical common knowledge in the field.

Biomarker

Lipids are principal components of cell membranes and also one of the three major nutrients together with proteins and sugars, and they are important biological molecules that serve both as efficient energy sources and as signaling molecules. Of the lipids, physiologically active lipids are called lipid mediators. A wide variety of fatty acid amides are known to function as lipid mediators, including arachidonylserine, arachidonamide and oleamide for example. Previous reports about oleamide have only concerned expression of such functions as (1) sleep induction, (2) CB1 receptor-mediated appetite regulation, (3) positive allosteric regulation of the serotonin 2C receptor, and (4) suppression of amyloid β deposition and the like. By contrast, the present disclosures concern the use of a fatty acid amide as a lipid mediator expressing a novel function, based on the discovery that fatty acid amides may functions as biomarkers for lifestyle diseases.

Fatty Acid Amide

Figure 1:
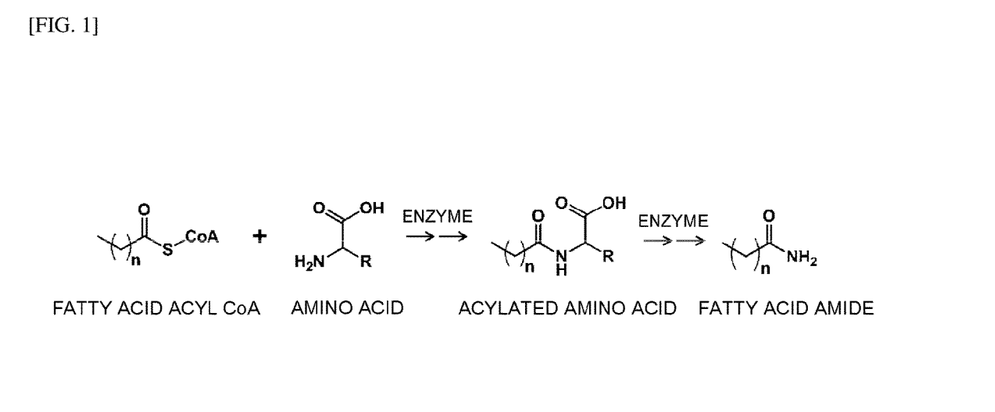
FIG. 1 is a drawing explaining the production of fatty acid amides in vivo.

Linear saturated fatty acids are produced from acetyl CoA (coenzyme A) and malonyl-CoA by fatty acid synthases in the bodies of microorganisms, plants, and animals including humans. The carbon numbers of fatty acids are increased in the endoplasmic reticulum and the like, and once fatty acid synthesis reaches a carbon number of 18 (stearic acid) for example, double bonds are produced in the center (ω-9 position) of the stearic acid, resulting in the production of the monovalent unsaturated fatty acid oleic acid in the body. These fatty acids are also catalyzed by acyl CoA synthase (ACS), and are converted into fatty acid acylates having thioester bonds (such as fatty acid acyl CoA) and activated as shown in FIG. 1. It is thought that these fatty acid acylates then react enzymatically with amino acids in the body to produce acylated amino acids, and that amide-type fatty acid amides are also formed by an enzymatic reaction. Fatty acid amides as biomarkers may include a wide range of such fatty acid amides derived from lipids in vivo, and derivatives of these.

As long as the amide part (—NH$_2$) of the fatty acid amide shown in FIG. 1 has in its chemical structure a monovalent functional group obtained by removing a hydrogen from ammonia or a monovalent amine or bivalent amine (that is, —NH$_2$ in the figure or —NHR or —NRR', wherein R and R' are hydrocarbon groups other than hydrogen), the rest of the specific structure is not particularly limited.

The fatty acid part of the fatty acid amide may be a long-chain fatty acid with 14 to 20 carbon atoms (hereunder sometimes shown as "C14 to C20") that occurs commonly in cells in vivo. These fatty acid parts are expressed by a combination of carbon number and number of double bonds in IUPAC biochemical nomenclature, and specific examples include C14:0 (myristic acid), 16:0 (palmitic acid), 16:1 (palmitoleic acid), 18:0 (stearic acid), 18:1(9) (oleic acid), 18:2(9,12) (linoleic acid), 18:3 (Δ9, Δ12, Δ15) (linolenic acid) and the like. Specific examples of fatty acid amides having these fatty acid parts include the fatty acid amides shown below.

[C1]

Myristic acid amide

Palmitic acid amide

Palmitoleic acid amide

Stearic acid amide

Oleic acid amide

Linoleic acid amide (f)

α-linolenic acid amide (g)

Arachidonic acid amide (h)

Various compounds are possible as the fatty acid amides disclosed here as long as they comprise amide parts bound to the fatty acid part consisting of oleic acid above. The tests of the inventors and others have confirmed that the in vivo concentrations of these fatty acid amides may all change significantly according to the progression of symptoms of lifestyle diseases. Of these fatty acid amides, the C16 and C18 long-chain fatty acid amides are especially suitable as biomarkers and the like because they are common in cells and are strongly associated with the progression of symptoms of lifestyle diseases. Specific examples of these long-chain fatty acid amides include oleic acid amide, linoleic acid amide, palmitoleic acid amide, palmitic acid amide and the like. Of these, oleic acid amide (oleamide) may be especially desirable.

In Vivo Concentrations of Fatty Acid Amides, and Diagnostic Method

In particular, although the details are unclear, the concentrations of fatty acid amides are negatively correlated with the glucose (blood sugar) concentrations of lifestyle disease patients in vivo. Thus, for example individuals with chronically high blood glucose concentrations have chronically lower concentrations of these fatty acid amides in their bodies than do individuals with normal glucose concentrations. In an individual who ordinarily has a normal blood glucose concentration, the fatty acid amide concentration in the body will not be reduced even if the blood glucose concentration becomes temporarily elevated. On the other hand, if in an individual with a chronically high blood glucose concentration achieves a temporary rise in fatty acid amide concentration in the body due to ingestion of food containing fatty acid amides for example, the fatty acid amide concentration in the body will fall again to a low level after several hours (such as 1 hour, or typically 4 hours). This tendency is not limited to blood in vivo, and the same phenomenon is also seen in organs and the like. For this reason, when the fatty acid amide concentration in a living body is low it can be inferred that the blood glucose concentration is chronically high in the same individual.

For purposes of diagnosis, a threshold value for distinguishing the fatty acid amide concentrations of healthy individuals and lifestyle disease patients may be established in advance based on in vivo fatty acid amide measurements from healthy individuals. When the in vivo fatty acid amide concentration of a test subject then falls below the threshold value, that subject can be diagnosed as suffering from a lifestyle disease.

As discussed below, in subjects in whom symptoms of lifestyle disease are progressing but who may not be diagnosed medically as completely suffering from a lifestyle disease, there is still a tendency for fatty acid amide concentrations to be lower than those of healthy subjects. Consequently, it is possible that a lifestyle disease could be evaluated based on in vivo concentrations of fatty acid amides during the early stages of the disease when recovery is relatively easy.

In analyzing the concentration of fatty acid amide or the like, "in vivo" may mean "in a sample taken from a living body".

Thus, in the technique disclosed here for example the threshold may be set at the highest fatty acid amide concentration within the range at which fatty acid amide levels can be judged to be significantly depressed in vivo in comparison with those of healthy subjects. Thus, for example subjects in which fatty acid amide concentrations are significantly depressed may be diagnosed or screened as a pre-lifestyle disease group in which progression of lifestyle disease is predicted, and encouraged to take preventative measures against lifestyle disease. Alternatively, they can be diagnosed or screened as a lifestyle disease intensive treatment target group in which the progress of lifestyle disease can be effectively prevented or ameliorated, and those lifestyle disease patients who may recover can be prioritized for treatment.

In Vivo Measurement of Fatty Acid Amide Concentrations

The biological material collected from a subject for purposes of measuring fatty acid amide concentrations may be any biological part containing bodily fluid, and may be for example a bodily fluid such as blood, tissue fluid or lymphatic fluid, or an organ or the like. Preferably it is blood (such as plasma or serum). These biological materials are preferably used in fatty acid amide measurement after total proteins in the bodily fluid have been removed.

The fatty acid amides may be assayed by for example colorimetric assay, gas chromatography (GC), gas chromatography-mass spectrometry (GC/MS), liquid chromatography-mass spectrometry (LC/MS), high-performance liquid chromatography-mass spectrometry (HPLC/MS), thin film chromatography (TLC) gel image analysis, capillary electrophoresis-time of flight mass spectrometry (CE-TOFMS), nuclear magnetic resonance spectroscopy (NMR) or the like. Particularly desirable is a LC-MS/MS method, in which components contained in a sample are isolated by chromatography, and a specific mass is selected with a quadrupole mass spectrometer and then detected with a time-of-flight type or quadrupole type mass spectrometer. This is desirable because, the LC-MS/MS method allows eight different fatty acids to be assayed comprehensively and accurately in one analysis (such as one injection).

When a liquid sample such as blood is taken as a biological sample, acetone as a protein precipitation agent can be added in the amount of about twice the liquid sample (such as serum or plasma) for example to precipitate out the proteins from the biological sample. The proteins are dissolved by the hydrophilic moieties being in contact with water in the blood, but when the water-soluble organic solvent acetone is added, the bonds between the proteins and the water molecules are broken and solubility is reduced. Thus, only the protein components of the biological sample are aggregated and precipitated in solution, leaving the soluble substances such as lipids in the blood. The method of precipitating the proteins is not limited to this, and for example another method such as known ammonium precipitation (salting out), trichloroacetic acid (TCA) precipitation, TCA/acetone precipitation or precipitation with methanol containing ammonium acetate may be adopted appropriately.

It is also undesirable for the liquid sample to contain other non-lipid components such as free sugars and amino acids. Therefore, the total lipids can also be isolated and extracted from the liquid sample by FOLCH or the like. Hydrogen bonds and hydrophobic bonds in the liquid sample can be weakened with a non-polar solvent such as ether, chloroform, benzene or hexane, while ion bonds can be weakened with a polar solvent such as highly polar methanol, ethanol or the like. Specifically, for example a mixed solution of chloroform and methanol (2:1) can be added to blood from which the proteins have been removed, and thoroughly stirred and then centrifuged to separate two layers, after which the supernatant part containing the chloroform, lipids and other lipid-soluble components can be collected and used as the measurement sample.

When an organ or other tissue sample has been collected as the biological sample, on the other hand, for example the collected tissue sample can be made into a uniform paste with a crusher or the like, and the tissue sample in paste form can be subjected to the protein separation and removal and lipid separation and extraction described above. The lipid separation and extraction method is not limited to the example given above, and various known methods such as the Bligh-Dyer method may also be used.

As is evident from the aforementioned methods for pretreating the biological sample, the fatty acid amides are detected as oleic acid (fatty acid) by these measurement methods. The LC-MS/MS column used and the other analysis conditions can be set appropriately according to the equipment used. For example, the eight kinds of fatty acid amides given above as examples of those that may be contained in the measurement sample may be assayed with reference to the LC-MS/MS analysis conditions disclosed in the examples below.

Use

That is, the following are made possible for example by the techniques disclosed here.

A biomarker for diagnosing a lifestyle disease is provided, wherein the biomarker includes a fatty acid amide in the living body.

The fatty acid amide may be oleamide for example.

In subjects suffering from lifestyle diseases or those who are not suffering from such diseases but in whom symptoms of such diseases have progressed, the concentrations of fatty acid amides in the body are significantly lower than in healthy subjects ($p<0.05$ for example). Consequently, by confirming that the fatty acid amide concentration in a living body is significantly lower than in a healthy subject, it is possible to diagnose that that body suffers from a lifestyle disease, or that the symptoms of a lifestyle disease have progressed. In other words, it is possible to diagnose not only lifestyle disease patients but also those in the pre-lifestyle disease group, and to take effective steps to combat or prevent lifestyle disease.

Fatty acid amide concentrations in the living body are correlated with concentrations of total blood cholesterol (T-Cho), low-density lipoprotein (LDL), glucose (blood sugar) and the like for example. The correlation with glucose is particularly high. Therefore, the lifestyle disease target may be at least one disease selected from obesity, dyslipidemia, fatty liver, diabetes and impaired glucose tolerance. Diabetes and dyslipidemia in particular can be diagnosed with a high degree of accuracy.

EXAMPLES

Some examples of the present invention are explained below, but not with the intent of limiting the invention to the matter shown in the examples.

1. Measuring Fatty Acid Amide Concentrations in Human Blood (High Blood Sugar)

Human blood samples were obtained by taking blood on an empty stomach from 81 patients who had visited the hospital for various reasons, and who had given informed consent (taken by Nagoya University Hospital). Serum was extracted from these blood samples, and the concentrations (mg/dL) of total cholesterol (T-Cho), neutral lipids (TG), low-density lipoprotein (LDL) and glucose were measured using a LABOSPECT 008 clinical automatic chemical analyzer manufactured by Hitachi High-Technologies Corporation. Based on these measurement results, subjects with blood glucose levels of less than 125 mg/dL were judged to be healthy subjects and the others were judged to be high blood sugar patients. Average values were calculated from the measurement values of the healthy subjects and the high blood sugar patients, respectively, as shown in Table 1 below. Of the 81 subjects, 55 were healthy subjects and 26 were high blood sugar patients.

Fatty acid amides were also assayed in the same blood samples. Specifically, the collected blood was centrifuged to obtain plasma. Ice-cooled acetone was added in the amount of twice the volume of the resulting plasma, which was then incubated for 30 minutes at $-20°$ C., after which the samples were centrifuged and the supernatant was collected to remove the proteins. A 2:1 chloroform:methanol solution was then added in the amount of 10 times the volume of the collected supernatant, and the mixture was thoroughly stirred and centrifuged, and the supernatant collected. This was supplied as the measurement sample to an ultra-performance liquid chromatography (LC-MS/MS) system, and fatty acid amides were identified and assayed.

The LC-MS/MS measurement conditions were as follows. The fatty acid amides that were assayed were myristic acid amide (C14:0), palmitic acid amide (C16:0), palmitoleic acid amide (C16:1), stearic acid amide (C18:0), oleic acid amide (C18:1), linoleic acid amide (C18:2), a-linolenic acid amide (C18:3) and arachidonic acid amide (C20:4). In this case, oleamide for example is detected at an LC retention time of 7.2 minutes and a mass-to-charge ratio (m/z) of 282 in the mass spectrum. During the assay, concentrations (μM) were calculated using a calibration curve prepared by the stable isotope dilution method using each fatty acid amide labeled with a stable isotope as an internal standard substance. The results are shown as a histogram in FIG. 2, separated into a healthy subject group and a high blood sugar patient group.

Equipment: ACQUITY UPLC-Xevo-TQD (Waters Corporation)
Mobile phase flow: 0.3 ml/min
Mobile phase: (A) 0.1% formic acid in water ($H_2O$)
(B) 0.1% formic acid in water+acetonitrile
Column: Develosil HB C30-UG-3 (2.0/100 mm) (Nomura Chemical Co., Ltd.)
Column heater temperature: 40° C.
Ionization mode: ESI-Positive, Cone 25 V, Collision 12 V
Analysis time: 15 minutes

TABLE 1

| Item | Healthy subjects (n = 33) | High blood sugar patients (n = 17) | P value |
|---|---|---|---|
| Age | 62.0 ± 1.86 | 62.0 ± 3.45 | 0.330 |
| T-Cho (mg/dL) | 194.05 ± 7.51 | 250.29 ± 3.35 | <0.001 |
| TG (mg/dL) | 140.69 ± 10.01 | 204.35 ± 11.0 | <0.001 |
| LDL (mg/dL) | 115.49 ± 5.66 | 155.65 ± 2.57 | <0.001 |
| Glucose (mg/dL) | 101.49 ± 1.95 | 188.65 ± 8.76 | <0.001 |
| Gender ratio (male:female) | 29:26 | 13:13 | — |

As shown in Table 1, the average measurement values for the hyperglycemic patient group were significantly higher than those of the healthy subject group for all items measured (T-Cho, TG, LDL, glucose).

Figure 2:
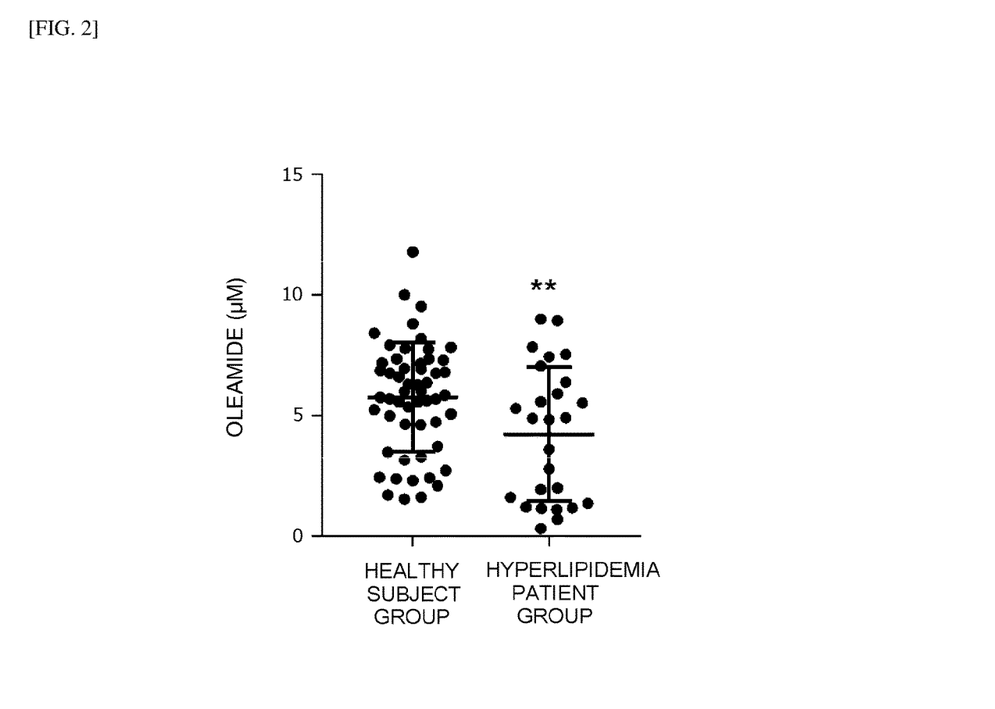
FIG. 2 is a histogram showing the results of measurement of serum oleamide concentrations, with results for a healthy subject group and a hyperlipidemia patient group shown separately.

On the other hand, the average measured values for fatty acid amides in blood were confirmed to be lower in the high blood sugar patient group than in the healthy subject group. Looking at oleamide in particular out of the eight fatty acid amides measured, the oleamide concentrations were much lower in the hyperglycemic patient group than in the healthy subject group. In FIG. 2, the differences between the blood oleamide concentrations of the healthy subject group and hyperglycemic patient group are shown as a scatter plot.

These results confirm that concentrations of fatty acid amides (such as oleamide) are significantly lower in the serum of hyperlipidemia patients. Consequently, it can be seen that this fatty acid amide can be used as a new biomarker for diagnosing lifestyle diseases for example.

2. Measuring Oleamide Concentrations in Human Blood (Diabetic Patients)

Human blood samples were obtained by taking blood on an empty stomach from 20 diabetic patients who had given informed consent (taken by Nagoya University Hospital). Serum was extracted from these blood samples and the concentrations (mg/dL) of glucose (blood sugar), low-density lipoprotein (LDL), neutral lipids (TG) and total cholesterol (T-Cho) and the concentration (μM) of oleamide in the serum were measured as before. As a result, a negative correlation was confirmed between serum glucose concentration and oleamide concentration in the diabetic patient group.

Figure 3A:
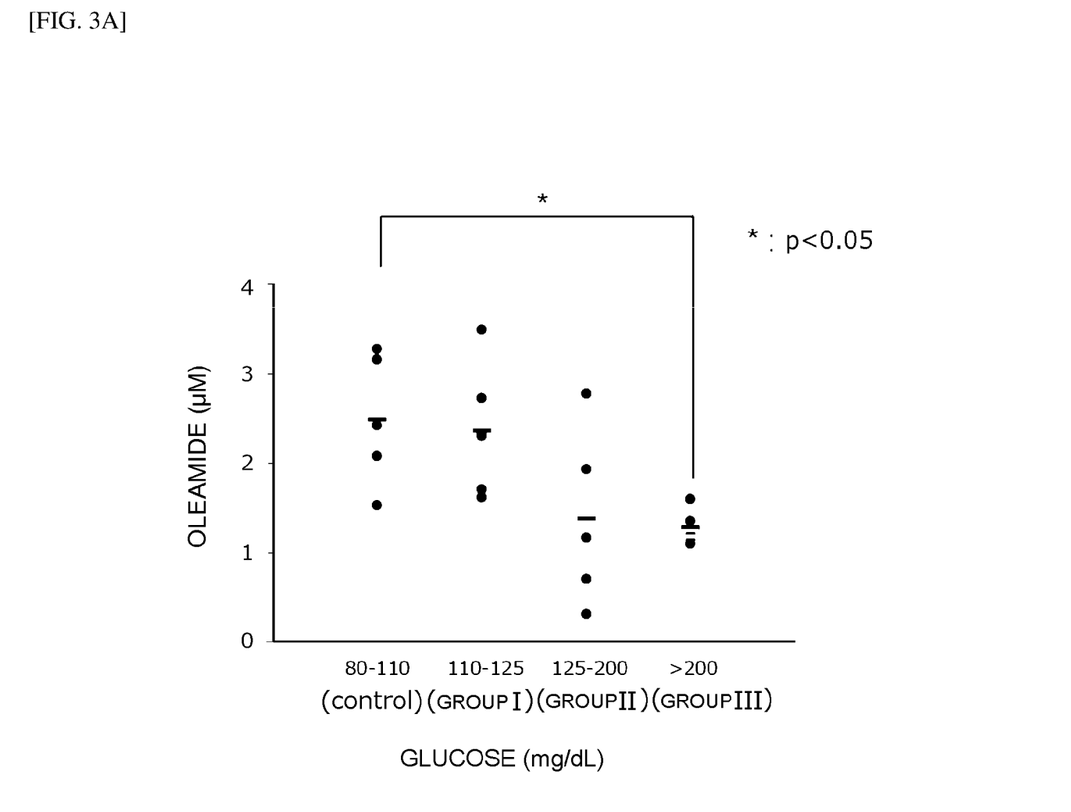
FIG. 3A is a histogram showing the results of measurement of serum oleamide concentrations in a group of diabetes patients, who were separated into four groups according to blood glucose concentration: at least 80 mg/dL and less than 110 mg/dL (control), at least 110 mg/dL and less than 125 mg/dL (Group I), at least 125 mg/dL and less than 200 mg/dL (Group II) and at least 200 mg/dL (Group III)
Figure 3B:
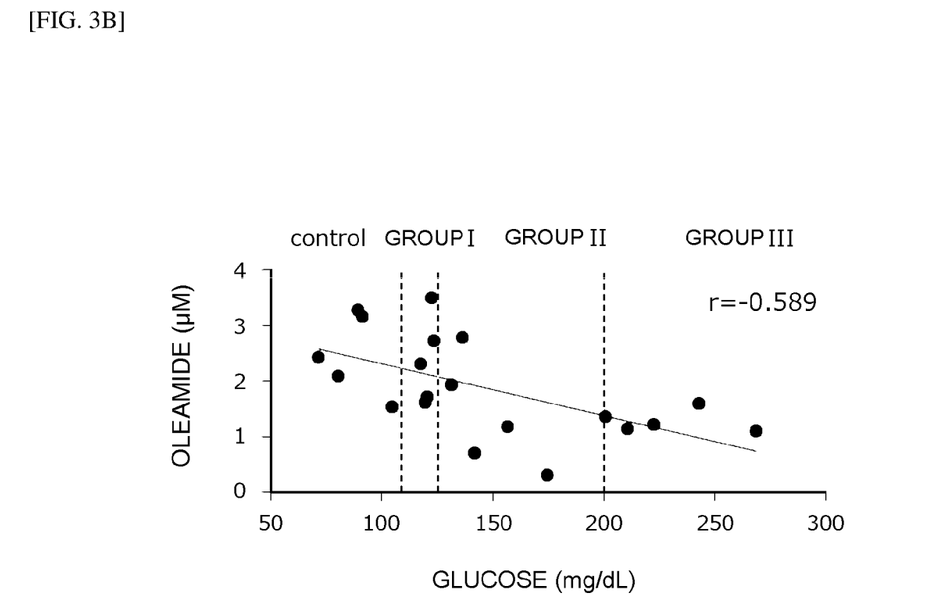
FIG. 3B is a scatter plot of the data from FIG. 3A.

The measurement results were then divided into four groups having blood glucose levels of at least 80 mg/dL and less than 110 mg/dL (control), at least 110 mg/dL and less than 125 mg/dL (Group I), at least 125 mg/dL and 200 mg/dL or less (Group II) and over 200 mg/dL (Group III), as shown in the histogram of FIG. 3A and the scatter plot of FIG. 3B.

The "control" is a group of patients with a fasting blood sugar of less than 110 mg/dL who were judged to be medically normal. "Group I" is a group of patients with a fasting blood sugar of at least 110 mg/dL and less than 125 mg/dL who were judged to be medically borderline. "Group II" and "Group III" are groups of patients with a fasting blood sugar of at least 125 mg/dL who were medically mostly judged to be diabetic. That is, in this test the fasting blood sugar levels that were classified as diabetic were divided into an early stage diabetes level (Group II) and a relative severe diabetes level (Group III, fasting blood sugar over 200 mg/dL).

As shown in FIG. 3A and FIG. 3B, as the blood glucose concentration rises there is an overall tendency for the oleamide concentration to decline. As shown in FIG. 3B, moreover, up through Group II the oleamide concentration drops dramatically as the glucose concentration rises. After dropping in Group II, however, the oleamide concentration remains largely unchanged in Group III.

Based on this, a patient in Group II who has been diagnosed with diabetes can be recommended for focused treatment if the patient's oleamide concentration is relatively high (such as 1.5 μM or more) since improvement and recovery from diabetes are judged to be relatively easy in such cases.

Moreover, if oleamide concentrations are found to be significantly depressed when measured during a regular checkup for example, diabetes can be said to have progressed and early treatment and prevention can be recommended even if the blood sugar levels are relatively low (such as fasting blood sugar of not more than 180 mg/dL, or especially not more than 150 mg/dL).

3. Measuring Oleamide Concentrations in Blood of Obesity Model Mouse

Five 6-week-old male ob/ob mice were used as an obesity model mouse group. Five 6-week-old male BALB/c normal mice were also used as a control mouse group. These mice were reared for 1 week, and blood was taken at 7 weeks.

Plasma was obtained by centrifugation from the collected blood as before. Ice-cooled acetone was added in the amount of twice the volume of the resulting plasma, which was then incubated for 30 minutes at −20° C., after which the samples were centrifuged and the supernatant was collected to remove the proteins. A 2:1 chloroform:methanol solution was then added in the amount of 10 times the amount of the plasma, and the mixture was thoroughly stirred and centrifuged, and the supernatant collected. This was supplied as the measurement sample to LC-MS/MS, and fatty acid amides were identified and assayed. Oleamide labeled with a stable isotope was used as an internal standard substance. The LC-MS/MS measurement conditions were the same as above. The measurement results for oleamide concentration are shown in FIG. 4, separately for the obese mouse group and the normal mouse group.

Figure 4:
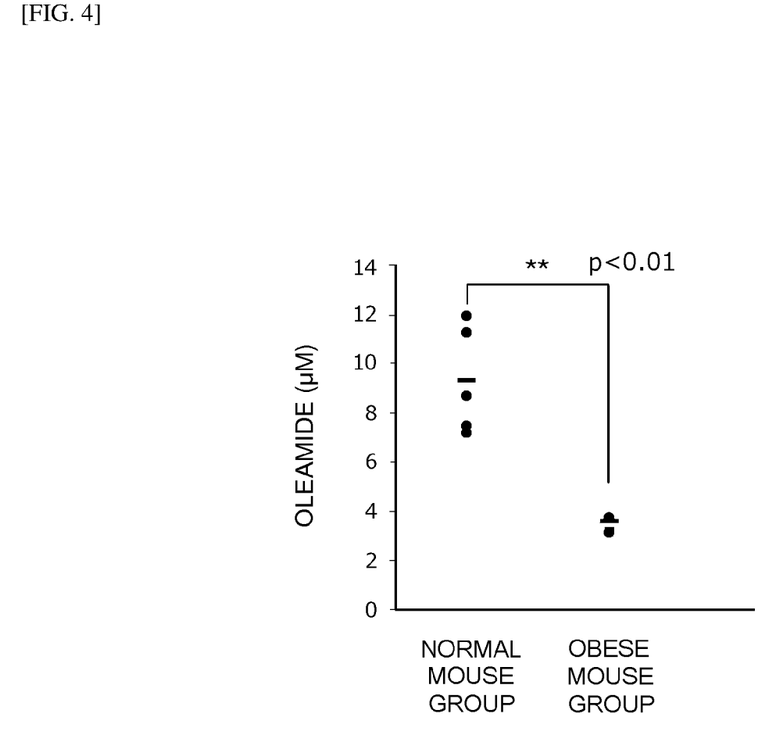
FIG. 4 is a histogram showing the results of measurement of serum oleamide concentrations in an obese mouse group and a normal mouse group.

As shown in FIG. 4, oleamide concentrations were significantly lower in the obesity model mice. This confirms that mice can be effective as an animal model for human disease, as far as the effects of oleamide are concerned. The oleamide level in the obesity model mice showed little variation between samples, so a model mouse could potentially be used to develop new methods for preventing, diagnosing and treating lifestyle diseases such as diabetes that are associated with the effects of oleamide.

Specific examples of the present invention were explained in detail above, but these are only examples, and do not limit the scope of the claims. The inventions disclosed here encompass various changes and modifications to the specific examples described above.

What is claimed is:

1. A method for diagnosing a lifestyle disease comprising:
preparing a measurement result of a concentration of a fatty acid amide obtained from a healthy subject;
collecting a biological sample from a subject;
measuring a concentration of the fatty acid amide contained in the biological sample; and
determining whether the subject suffers from a lifestyle disease or a lifestyle disease has progressed when a measured value of the concentration of the fatty acid amide obtained from the subject is lower than the measurement result obtained from the healthy subject.

2. The method for diagnosing a lifestyle disease according to claim 1, wherein the biological sample is an organ or blood.

3. The method for diagnosing a lifestyle disease according to claim 1, wherein the concentration of the fatty acid amide is measured by liquid chromatography-mass spectrometry.

4. The method for diagnosing a lifestyle disease according to claim 3, wherein the liquid chromatography-mass spectrometry includes
isolating two or more components contained in the biological sample by liquid chromatography,
ionizing the isolated components and selecting a specific mass component with a quadrupole mass spectrometer, then dissociating the specific mass component, and
detecting the dissociated component with a mass spectrometer.

5. The method for diagnosing a lifestyle disease according to claim 1, wherein the lifestyle disease is at least one selected from the group consisting of obesity, dyslipidemia, diabetes and impaired glucose tolerance.

6. The method for diagnosing a lifestyle disease according to claim 1, wherein the fatty acid amide is oleamide.

* * * * *